United States Patent [19]

Langmaid

[11] Patent Number: Plant 6,978

[45] Date of Patent: Aug. 8, 1989

[54] ILEX×ALTACLERENSIS 'WIGHT SELECTION' VARIETY

[75] Inventor: Martin C. Langmaid, Cairo, Ga.

[73] Assignee: Weyerhaeuser Company, Tacoma, Wash.

[21] Appl. No.: 153,734

[22] Filed: Feb. 8, 1988

[51] Int. Cl.[4] ..... A01H 5/00

[52] U.S. Cl. ..... Plt./65

[58] Field of Search ..... Plt./65

*Primary Examiner*—Robert E. Bagwill

[57] ABSTRACT

A new and distinct variety of *Ilex×altaclerensis* having outstanding tolerance to very high southern day and night temperatures while retaining USDA Zone 8 winter hardiness.

3 Drawing Sheets

The present invention relates to a new and distinct plant cultivar of *Ilex×altaclerensis* in the Aquifoliaceae family.

This new Ilex selection, hereafter referred to as 'Wight Selection' appears to be a hybrid of *I. aquifolium×I. perado* subsp. platphylla, commonly known as 'High Clere Holly.' The mother plant was discovered in early 1980 at Wight Nursery, Highway 111 South, Cairo, Ga., growing in a purchased lot of *Ilex×koehneana* 'Wirt L. Winn.' *Ilex×koehneana 'Wirt L. Winn'* is itself a hybrid of *I. aquifolium×I. latifolia.*

The current new cultivar Ilex 'Wight Selection' appeared quite different from the other plants in the block. After isolation and further evaluation, samples were submitted to and identified by Mr. Gene Eisenbeiss (Registrar Authority, Holly Society of America, U.S. National Arboretum, Washington, D.C.) as a cultivar of *Ilex×altaclarensis.*

This new cultivar has been reproduced numerous times by asexual propagation (vegetative cuttings). Each of the progeny exhibits identical characteristics of the original mother plant establishing this selection as reproducible and true to type.

Ilex 'Wight Selection' has many desirable and distinctive characteristics which render it unique from any other potentially similar *Ilex×altaclerensis* or *Ilex aquifolium* cultivar presently offered in the nursery trade. The unique ability of this distinct selection to withstand high summer temperatures and especially high night temperatures of the Southeast without damage is the most significant desirable characteristic. Other distinct characteristics of Ilex 'Wight Selection' include variability of spines of the leaf margins, distinct purple pigmentation of the young leaves and stems and bright red fruit which is born in moderate quantities.

BRIEF DESCRIPTION OF THE PHOTOGRAPHS

DETAILED PLANT DESCRIPTION

The following is a detailed description of the performance and appearance of Ilex 'Wight Selection.' Descriptions are based on no fewer than 15 specimens for each specified characteristic. Color determinations and comparisons are all based on The Royal Horticultural Society Colour Chart.

Overall size and growth habit:

*Size.*—The ultimate size of Ilex 'Wight Selection' is unknown as no specimen has reached full maturity. The growth rate is between 30 cm to 45 cm (1 foot to 1½ foot) per year.

Figure 1:
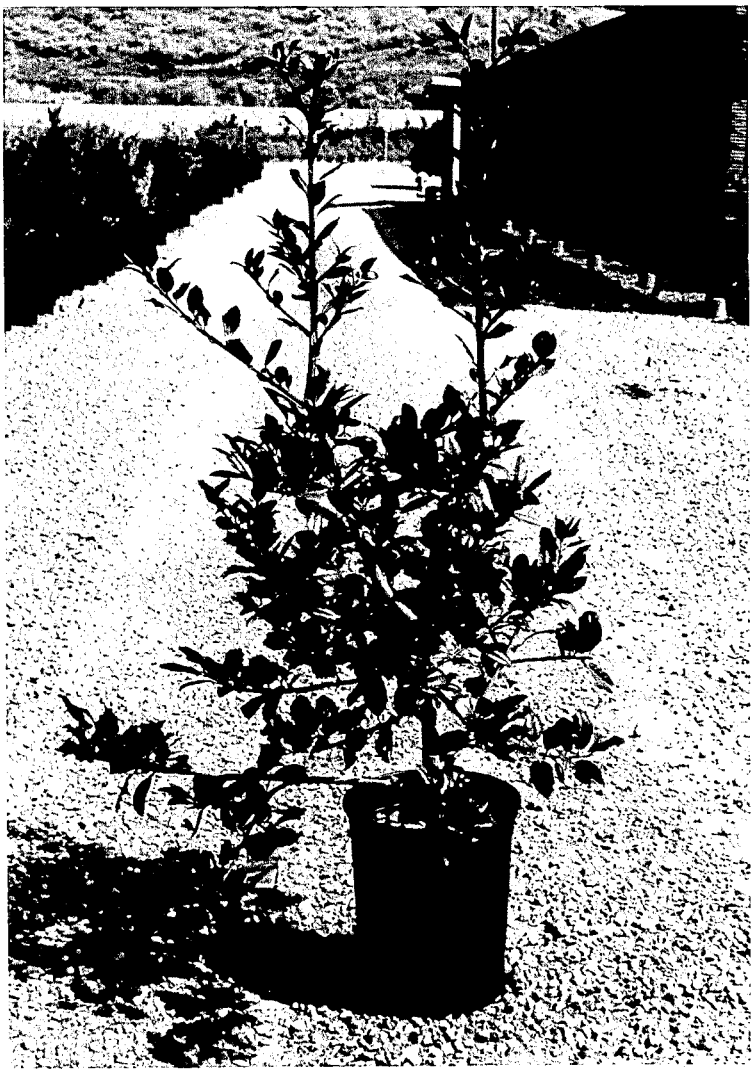
FIG. 1 shows an unpruned individual plant of the new selection growing in a 19 L (5 gallon) container of an age of 27 months from cutting.

*Habit.*—Upright, pyramidal, somewhat open, well branched (FIG. 1).

Figure 2:
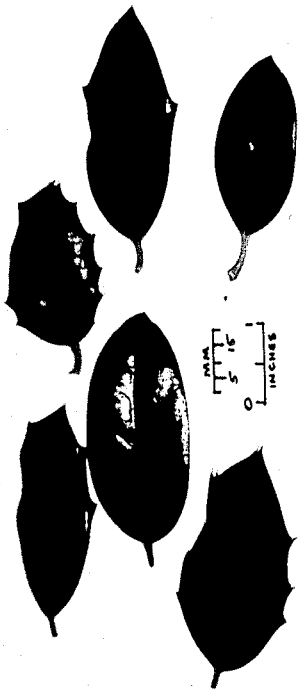
FIG. 2 is a side-by-side comparison of leaves taken from one plant showing the variability of spines on the leaf margin.

Foliage:

*Size.*—Length (from petiole to leaf apex) — 6.1 cm to 8.2 cm (2¼ to 3½ in.). Width — 2.6 cm to 4.2 cm (1 to 1¾ in.). Margins — Entire or with 1 to 16 spines (FIG. 2). Shape — Ovate to oblong — lanceolate. Apex — Acute-cuspidate (with single spine at the tip). Base — Obtuse. Petioles — 1 to 1.5 cm. (0.4 to 0.6 in.).

Figure 3:
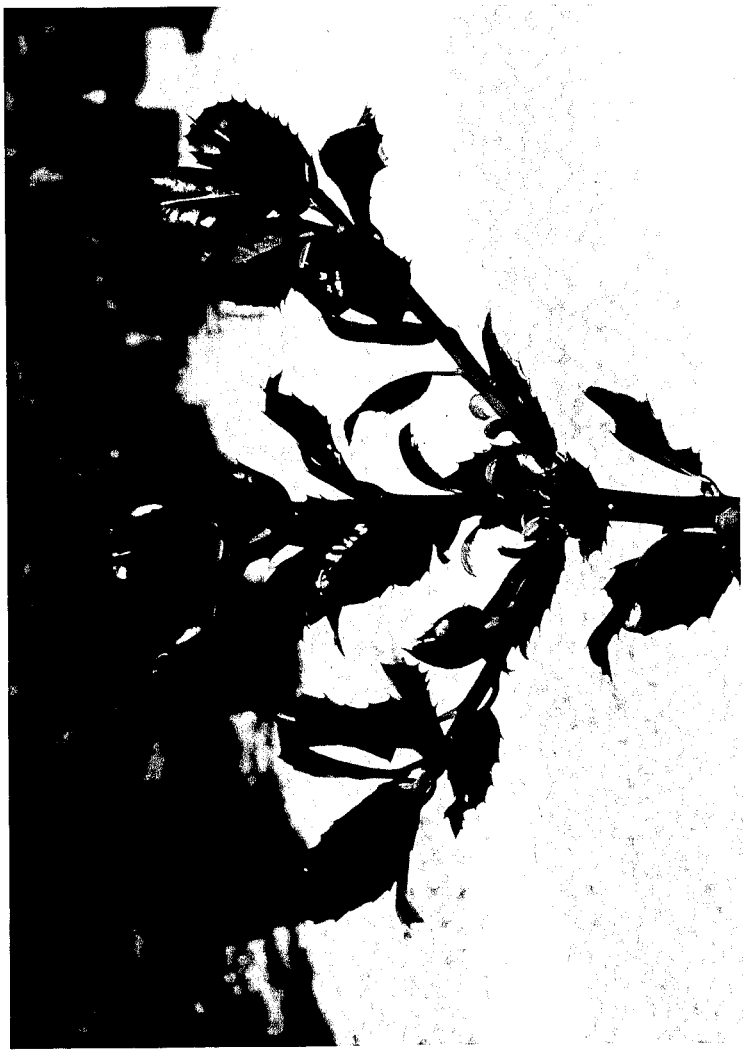
FIG. 3 shows the winter color of young (immature) leaves and stems.

*Color.*—Winter color — Upper leaf surface of young (immature) leaves: R.H.S. Colour Chart Fan 4, Greyed-Purple Group, No. 187A (FIG. 3). Lower leaf surface of young (immature) leaves: R.H.S. Colour Chart Fan 4, Greyed-Purple Group, No. 183B (FIG. 3). Upper leaf surface of mature leaves: R.H.S. Colour Chart Fan 3, Green Group, No. 139A. Lower leaf surface of mature leaves: R.H.S. Colour Chart Fan 3, Green Group, No. 137B. Summer Color — Upper leaf surface of young (immature) leaves: R.H.S. Colour Chart Fan 3, Green Group, No. 141B. Lower leaf surface of young (immature) leaves: R.H.S. Colour Chart Fan 3, Green Group, No. 146C. Upper leaf surface of mature leaves: R.H.S. Colour Chart Fan 3, Green Group, No. 139A. Lower leaf surface of mature leaves: R.H.S. Colour Chart Fan 3, Green Group, No. 137C.

Stem color:

*Winter color.*—Newly emerging and young undeveloped stems: R.H.S. Colour Chart Fan 4, Greyed-Purple Group, No. 183B (FIG. 3). Mature stem (one to two years growth): R.H.S. Colour Chart Fan 3, Yellow-Green Group, No. 146A.

*Summer color.*—Newly emerging and young undeveloped stems: R.H.S. Colour Chart Fan 3, Yellow-Green Group, No. 146C. Mature stem (one to two years growth): R.H.S. Colour Chart Fan 3, Yellow-Green Group, No. 148A.

Inflorescence and fruit:

*Flowers.*—Pistillate, in terminal clusters born on the preceding season's growth. Four petals.

*Size.*—Fully open blooms are 7 to 11 mm. in diameter.

*Petal color.*—R.H.S. Colour Chart Fan 4, White Group No. 155C.

*Fruit.*—Round 8 to 10 mm in diameter; formed in moderate quantities.

*Fruit color.*—R.H.S. Colour Chart Fan 1, Red Group No. 44A. Produced in September and attaining full coloration by December.

Environmental tolerances:

*Heat tolerance.*—Ilex 'Wight Selection' has the unique ability to withstand high summer day and night temperature at Cairo, in southwestern Georgia without damage. Production trials of *Ilex aquifolium* 'San Gabriel' and Ilex 'Wight Selection' were carried out in 1985 at Wight Nursery, Cairo, Ga. Summer high temperatures averaged in mid nineties (degrees F.) with an average humidity usually exceeding 50%. The average nighttime low temperatures averaged in the seventies (degrees F.). During the peak high temperatures of this period of time all of the Ilex 'San Gabriel' exhibited general foliage deterioration which finally led to their mortality while the Ilex 'Wight Selection' were unaffected. According to Mr. Gene Eisenbeiss (Holly Society of America, U.S. National Arboretum, Washington, D.C.) "In spite of the many cultivars of *I. aquifolium* and the hybrid altaclerensis, few perform well anywhere on the East Coast particularly south of Washington, D.C. They all seem to have a difficult time with the high summer temperatures especially high night temperatures."

*Hardiness.*—Ilex 'Wight Selection' survived 39 hours at less than 20° F. in Cairo, Ga., from 12/21/84 to 1/4/84. Ilex 'Wight Selection' survived 39 hours at less than 20° F., and 84 hours at less than 32° F., from 1/2/85 to 1/4/85. The minimum cold temperature in 1985 was 9° F. Wight Nursery, Cairo, Ga. is located in USDA Hardiness Zone 8, (10° to 20° F., −12.2° to −6.7° C.). *Ilex aquifolium:* USDA Zone 6 (−10° to 0° F., (−23.3° to 17.8° C.). Ref., John J. Sabuco, *The Best of the Hardiest,* 2nd edition. *Ilex×altaclerensis:* USDA Zone 6 (−10° to 0° F., −23.3° F., to 17.8° C.). Ref., Carl Whitcomb, *Know It and Grow It. Ilex perado:* USDA Zone 7 (0° to 10° F., −17.8° to −12.2° C.). Ref., Baily, *Hortus Third. Ilex latifolia:* USDA Zone 7 (0° to 10° F., −17.8° to −12.2° C.). Ref., Carl E. Whitcomb, *Know It and Grow It.*

COMPARISON WITH THE MOST SIMILAR CULTIVARS

*Ilex×altaclerensis* 'Camellifolia'

Leaf size: To 12.7 cm (5") long and 5.1 cm (2") wide, larger than Ilex 'Wight Selection.'

Leaf margins: Essentially entire or with erratic spines from 1 to 8, rarely armed on both margins. Fewer spines than 'Wight Selection' and Ilex 'Wight Selection' has spines on entire margins on some leaves.

Plant habit: Pyramidal, similar to the Ilex 'Wight Selection.'

Fruit: Fruits abundantly, 'Wight Selection' fruits in moderation.

*Ilex×*'Nellie R. Stevens'

Leaf size: To 10.2 cm (4") long and 3.8 cm (1.5") wide, with a bullate appearance which differs from Ilex 'Wight Selection.'

Leaf margins: Entire or 2 to 3 spines on each side of the leaf.

Plant habit: Pyramidal, similar to the Ilex 'Wight Selection.'

Fruit: Heavily fruitful, in contrast to the new selection.

*Ilex×koehneana* 'Wirt L. Winn'

Leaf size: To 6.3 cm (2.5") long and 3.8 cm (1.5") wide, oval leaves. Ilex 'Wight Selection' has ovate to oblong-lanceolate leaves.

Leaf margins: Very spiny compared to Ilex 'Wight Selection.'

Plant habit: Similar pyramidal form to Ilex *Wight Selection.*'

Fruit: Fruits more heavily than Ilex 'Wight Selection.'

REFERENCES

Andrews, S., 1986. More notes on Clones of *Ilex×altaclerensis. Holly Society Journal.* 4(3): 9–17.

Baily, L. H., 1976. *Hortus Third,* McMillan, New York.

Dirr, M., 1983. *Manual of Woody Landscape Plants:* Their Identification, Ornamental Characteristics, Culture, Propagation and Uses. Stipes Publishing Co. Champaign, Ill.

Hillier Nurseries, 1984. *Manual of Trees & Shrubs,* 5th Ed., Ampfield House, Ampfield, Romsey, U.K.

Krussmann, G., 1985. *Manual of Cultivated Broad-Leaved Trees & Shrubs,* Volume 11, E-PRO. Timber Press, Portland, Oreg.

Sabuco, J., 1987. *The Best of the Hardiest,* 2nd Edition. Good Earth Publishing, Ltd. Flossmore, Ill.

Whitcomb, C., 1985. *Know It and Grow It,* 11, Lacebark Publications, Stillwater, Okla.

Dengler, H., T. R. Dudley and G. K. Eisenbeiss, 1970. *Handbook of Hollies* American Horticultural Magazine, 49(4): 164–170.

I claim:

1. A new and distinct variety of *Ilex×altaclerensis* substantially as shown and described, characterized by:

a. having ovate to oblong-lanceolate leaves with a length generally in the range of 60–82 mm long and 26–42 mm wide with about 1–16 marginal spines, b. a round fruit 8–10 mm in diameter produced only in moderate quantities, and c. an outstanding tolerance to summer day temperatures exceeding 90° F. and night temperatures often exceeding 70° F. while having a cold hardiness at least suitable for USDA Zone 8 (10°–20° F.).

* * * * *

ILEX
WIGHT SELECTION